(12) United States Patent
Tsuji

(10) Patent No.: US 6,355,690 B1
(45) Date of Patent: Mar. 12, 2002

(54) REMEDY FOR CAG REPEAT EXPANSION DISEASES

(75) Inventor: Shoji Tsuji, Niigata (JP)

(73) Assignee: Niigata University (JP)

( * ) Notice: Subject to any disclaimer, the term of this patent is extended or adjusted under 35 U.S.C. 154(b) by 0 days.

(21) Appl. No.: 09/236,002

(22) Filed: Jan. 22, 1999

(30) Foreign Application Priority Data

Jan. 26, 1998 (JP) ............................................ 10-027739

(51) Int. Cl.$^7$ .......................................... A61K 31/095
(52) U.S. Cl. ..................................... 514/706; 514/740
(58) Field of Search .................................. 514/706, 740

(56) References Cited

U.S. PATENT DOCUMENTS

| 4,929,630 A | 5/1990 | Castelhano et al. | ......... 514/380 |
| 5,725,870 A | * 3/1998 | Thoene | ....................... 424/433 |

FOREIGN PATENT DOCUMENTS

| WO | WO 93/06832 | | 4/1993 |
| WO | WO 93/18760 | | 9/1993 |
| WO | 95/10268 | * | 4/1995 |
| WO | 96/06181 | * | 2/1996 |
| WO | WO 98/04245 | | 2/1998 |
| WO | 98/04245 | * | 2/1998 |

OTHER PUBLICATIONS

The Merck Index (Twelfth Edition), p. 470, Jan. 1996.*
Fluka Catalog, p. 446, Jan. 1995.*
Jokay et al., "S–methylthio–cysteine and cystamine are potent stimulators of thiol production and gluthathione synthesis", Life Sci., vol. 62(2), PL27–PL33, 1997.*
Vladimirov et al., "The influence of cystamine on the level of post–radiation peroxidation products in the lymph of dogs", Radiats. Biol., Radioekol., vol. 37(1): 56–60, 1997.*
Newton et al., "Effect of polyamine–induced compaction and aggregation of DNA on the formation of radiation–induced strand breaks: quantitative models for cellular radiation damage", Radiat, Res., vol. 148(3): 272–284, 1997.*
Lukashin et al., "Radioprotectant action of cystamine and heparin in rats with different resistance", Byull. Eksp. Biol. Med., vol. 121(5): 544–546, 1996.*
Ho et al., "Cystamine inhibits HIV type 1 replication in cells of monocyte/macrophage and T–cell lineages", AIDS Res. Hum. Retroviruses, vol. 11(4): 451–459, 1995.*
Yancey et al., "Evaluation of monodansylcadaverine for effects on tumor growth", J. Natl. Cancer Inst., vol. 52(3): 733–735, 1974.*
Cooper et al., "Transglutaminase–catalyzed inactivation of glyceraldehyde 3–phosphate dehydrogenase and alpha–ketoglutarate dehydrogenase complex by polyglutamine domains of pathological length", Proc. Natl. Acad. Sci, USA, vol. 94(23): 12604–12609, 1997.*

Bates et al., "Transgenic mouse models of neurodegenerative disease caused by CAG/polyglutamine expansions", Molecular Medicine Today, vol. 3(11): 508–515, Nov. 1997.*

Fischer, K.M., "Etiology of (CAG)n triplet repeat neurodegenerative diseases such as Huntingdon's disease is connected to stimulation of glutamate receptors", Medical Hypotheses, vol. 48(5): 393–398, May 1997.*

Cooper et al., *J. Neurochem.*, 69: 431–4 (1997).

Cariello et al., *Hum. Genet.*, 98: 633–5 (1996).

Partial European Search Report dated Oct. 13, 2000.

Shuichi Igarashi et al., "Suppression of Aggregate Formation and Apoptosis by Transglutaminase Inhibitors in Cells Expressing Truncated DRPLA Protein with an Expanded Polyglutamine Stretch", Nature Genetics, vol. 18, pp. 111–117, Feb. 1998, Macmillan Publishers, USA.

Lucio Cariello et al., "Transglutaminase Activity is Related to CAG Repeat Length in Patients with Huntington's Disease", Human Genetics, (1996) 98:633–635, Springer–Verlag, Berlin, Germany.

P. Kahlem et al., "Peptides Containing Glutamine Repeats as Substrates for Transglutaminase–Catalyzed Cross–Linking: Relevance to Diseases of the Nervous System", Proc. Natl. Acad. Sci., vol. 93, pp. 14580–15485, Dec. 1996, The National Academy of Sciences of the United States of America, USA.

Arthur J.L. Cooper et al., "Polyglutamine Domains are Substrates of Tissue Transglutaminase: Does Transglutaminase Play a Role in Expanded CAG/Poly–Q Neurodegenerative Diseases?", Journal of Neurochemistry, vol. 69, pp. 431–434, (1997), Lippincott–Raven Publishers, Philadelphia, Pennsysvania, USA.

* cited by examiner

Primary Examiner—Gary Geist
Assistant Examiner—Leigh C. Maier
(74) Attorney, Agent, or Firm—Burns, Doane, Swecker & Mathis, LLP

(57) ABSTRACT

To elucidate the molecular mechanisms of "gain of toxic function" of expanded polyglutamine stretches in CAG repeat expansion diseases, the inventors established an expression system of full-length and truncated cDNAs for dentatorubral-pallidoluysian atrophy (DRPLA) and found that truncated DRPLA proteins containing the expanded polyglutamine stretch, but not the full-length protein, form peri- and intra-nuclear aggregates consisting of filaments and concomitant apoptosis. The apoptotic cell death was partially suppressed by transglutaminase inhibitors, cystamine and monodansyl cadaverine, raising the possibility of involvement of transglutaminase reaction. The results may provide a potential basis for the development of therapeutic measures for CAG repeat expansion diseases.

3 Claims, 14 Drawing Sheets

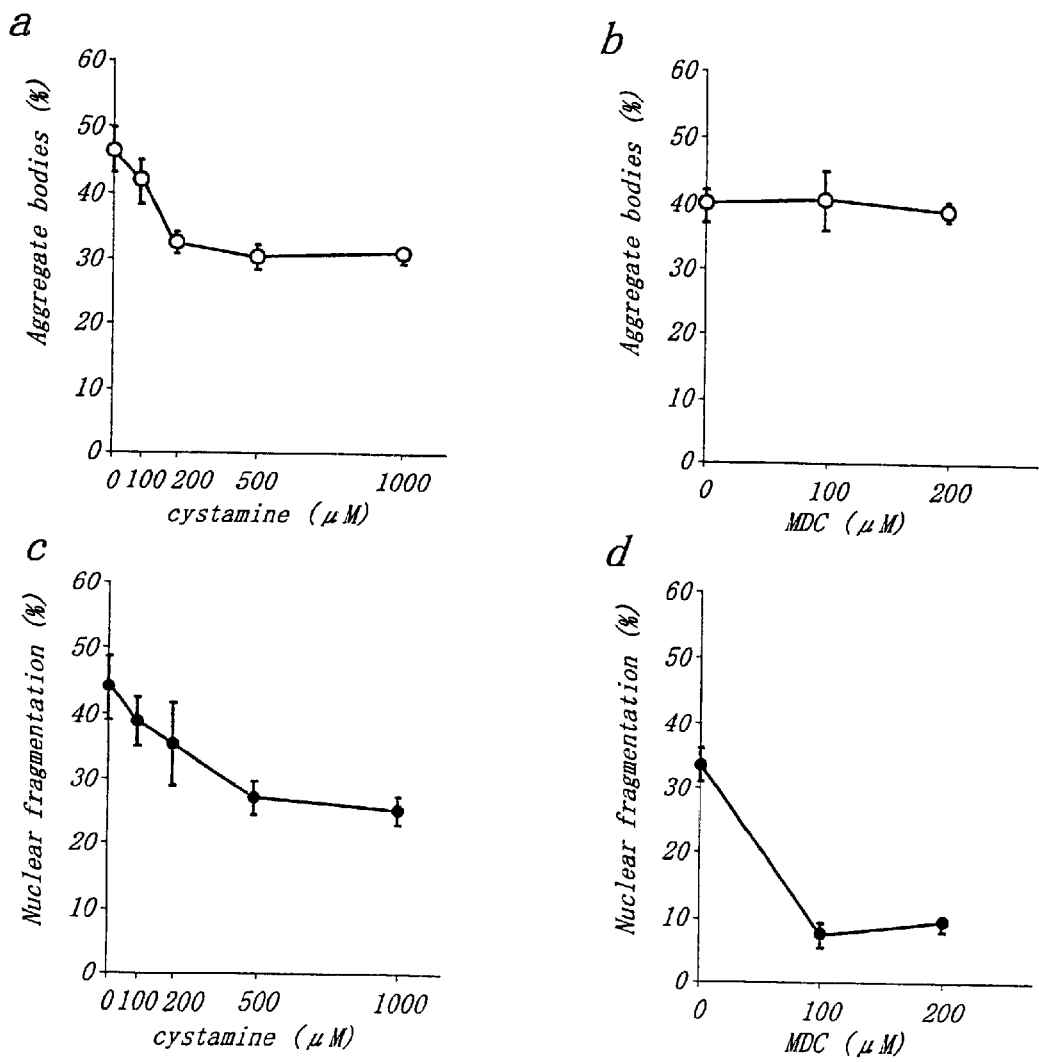
FIG_8

REMEDY FOR CAG REPEAT EXPANSION DISEASES

TECHNICAL FIELD

This invention is related to a remedy for a CAG repeat expansion disease.

BACKGROUND ART

Expansion of CAG trinucleotide repeats coding for polyglutamine stretches has been identified as a common pathogenic mutation for eight neurodegenerative diseases including spinal and bulbar muscular atrophy (SBMA)[1], Huntington disease (HD)[2], spinocerebellar ataxia type1 (SCA1)[3], dentatorubral-pallidoluysian atrophy (DRPLA)[4,5], Machado-Joseph disease (MJD)[6], SCA2[7-9], SCA6[10] and SCA7[11], and the number of diseases caused by the same mechanism is expected to increase further. There are many common features shared among these diseases; 1. The central nervous system is commonly affected with distinct distributions of neuronal loss, which are unique to each disorder. 2. Considerable heterogeneities of the clinical presentations even within the same pedigree, which are a function of the size of expanded CAG repeats. 3. Genetic anticipation i.e. accelerated age at onset in successive generations, which is also a result of intergenerational increase in the size of expanded CAG repeats.

There are no common homologous domains shared among the gene products except for the polyglutamine stretches[1-14], and the gene products of the mutant genes have been shown to be expressed at levels comparable to those of wild-type genes[15-18]. These observations raise the possibility that the polyglutamine stretch itself exerts a "gain of toxic function". In accordance with this, transgenic mice harboring a full-length SCA1 cDNA containing an expanded CAG repeat under control of the L7 promoter have been shown to exhibit cerebellar ataxia and degeneration of Purkinje cells in the cerebellum[19]. More interestingly, transgenic mice carrying mostly the expanded CAG repeat of the MJD1 gene[20] or exon 1 of huntingtin gene containing the expanded CAG repeat have also been demonstrated to exhibit neurological phenotypes and neurodegeneration. Very recently it has been demonstrated that mice transgenic for exon 1 of the HD gene carrying expanded CAG repeats develop neuronal intranuclear inclusions[22]. The toxicity of a peptide containing mostly the expanded polyglutamine stretch of MJD1 protein has also been demonstrated in a transient expression system using COS cells[20]. Thus, evidence which indicates that expanded polyglutamine stretches have toxic functions is accumulating.

Various hypotheses have been proposed to explain the mechanisms of the toxicity of expanded polyglutamine stretches. Perutz and the colleague proposed that polyglutamine stretches may function as polar zippers by joining complementary proteins through hydrogen bondings, and that extensions of the polyglutamine stretches may result in strong joining and aggregation of the affected proteins[23,24]. Another intriguing hypothesis has recently been proposed by Kahlem et al.[25]. They proposed that proteins with expanded polyglutamine stretches may serve as better substrates for transglutaminase than wild-type proteins, and that expanded polyglutamine stretches preferentially become cross-linked with polypeptides containing lysyl groups to form covalently bonded aggregates. However, the following questions has not elucidated yet. 1. Do the full-length or truncated proteins with expanded polyglutamine stretches form aggregates and exhibit cytotoxicity? and 2. Are transglutaminases involved in the formation of aggregates or in cytotoxicity? Moreover, there is no information on means for alleviate the cytotoxicity of the mutant proteins. Therefore, there has been no remedy for CAG repeat expansion diseases.

SUMMARY OF THE INVENTION

The object of this invention is to elucidate the molecular mechanism of "gain of toxic function" caused by polyglutamine stretch at CAG repeat expansion diseases and thus to provide the therapeutic remedy for CAG repeat expansion diseases. That is, a CAG repeat exists on a protein coding region and encodes polyglutamine stretches. Increase in the size of CAG repeat causes longer polyglutamine stretch, and as the result, it comes to exhibit cytotoxicity. Elucidation of the mechanism to cause cytotoxicity and establishment of the means to moderate cytotoxicity enable to develop a remedy for CAG repeat expansion disease. The object of this invention is to develop the therapeutic measures for CAG repeat expansion diseases through such kind of approach.

To address these questions, the inventors established an expression system of full-length and truncated cDNAs for dentatorubral-pallidoluysian atrophy (DRPLA) and found that truncated DRPLA proteins containing the expanded polyglutamine stretch, but not the full-length protein, form peri- and intra-nuclear aggregates consisting of filaments and induce concomitant apoptosis. Moreover, formation of the aggregates was found at cerebellar dentate nucleus of all DRPLA patients examined. That is, the relationship between truncated DRPLA protein and DRPLA was found.

The effect of various transglutaminase inhibitors was examined to elucidate the involvement of transglutaminase on the aggregation formation and apoptotic cell death. As the result, some transglutaminase inhibitors were found to inhibit the aggregate formation and apoptotic cell death. Then involvement of transglutaminase on DRPLA was confirmed.

The series of results revealed that transglutaminase inhibitors are available as a remedy for CAG repeat expansion diseases including DRPLA. In short, this invention relates to the use of transglutaminase inhibitors for treating CAG repeat expansion diseases. In preferred embodiments, (1) A remedy for a CAG repeat expansion disease containing a transglutaminase inhibitor as its active ingredient.

(2) The remedy as described in (1), wherein the transglutaminase inhibitor is selected from a group consisting of cyctamine and monodansyl cadaverine.

(3) The remedy as described in (1) wherein the CAG repeat expansion disease is selected from a group consisting of: spinal and bulbar muscular atrophy, Huntington disease, spinocerebellar ataxia type1, dentatorubral-pallidoluysian atrophy, Machado-Joseph disease, spinocerebellar ataxia 2, spinocerebellar ataxia 6 and spinocerebellar ataxia 7.

(4) The remedy as described in (2) wherein the CAG repeat expansion disease is selected from a group consisting of: spinal and bulbar muscular atrophy, Huntington disease, spinocerebellar ataxia type1, dentatorubral-pallidoluysian atrophy, Machado-Joseph disease, spinocerebellar ataxia 2, spinocerebellar ataxia 6 and spinocerebellar ataxia 7.

(5) A pharmaceutical composition for treating a CAG repeat expansion disease: comprising
a transglutaminase inhibitor as its active ingredient, and a pharmaceutically accepted ingredients for formulation.

(6) The pharmaceutical composition as described in (5), wherein the transglutaminase inhibitor is selected from a group consisting of cyctamine and monodansyl cadaverine.

(7) The pharmaceutical composition as described in (5) wherein the CAG repeat expansion disease is selected from a group consisting of: spinal and bulbar muscular atrophy, Huntington disease, spinocerebellar ataxia type1, dentatorubralpallidoluysian atrophy, Machado-Joseph disease, spinocerebellar ataxia 2, spinocerebellar ataxia 6 and spinocerebellar ataxia 7.

(8) The use of a transglutaminase inhibitor for manufacturing a pharmaceutical composition for treating a CAG repeat expansion disease.

(9) The use as described in (8) wherein the transglutarninase inhibitor is selected from a group consisting of cystamine and monodansyl cadaverine.

This invention relates to a remedy for CAG repeat expansion diseases wherein the effective ingredients are transglutaminase inhibitors. The therapeutic target of this invention includes spinal and bulbar muscular atrophy, Huntington disease, spinocerebellar ataxia type1, dentatorubral-pallidoluysian atrophy, Machado-Joseph disease, SCA2, SCA6 and SCA7.

There is no limitation for the effective ingredients of this invention such as cystamin or MDC, so far as they have inhibitory effect on transglutaminase activity. The remedy of this invention can be formulated by conventional methods, so far as transglutaminase inhibitors are used as its effective ingredients. Other ingredients for formulation includes, for example, pharmacologically accepted carriers or media such as saline, sterilized water, a plant oil, an emulsifier, a suspension agent and stabilizer, but the ingredients are not to be limited to them. It is possible to medicate the remedy of this invention to patients of CAG repeat expansion diseases by conventional methods such as arterial injection, intravenous injection, hypodermic injection.

BRIEF DESCRIPTION OF THE DRAWINGS

FIG. 8 shows effects of cystamine and monodansyl cadaverine (MDC) on the aggregate formation and apoptotic cell death of COS7 cells transfected with pEGFP-$Q_{82}$-19. COS7 cells transfected with pEGFP-$Q_{82}$-19 were cultured in various concentrations of cystamine (a, c) or MDC (b, d), and assayed for aggregate formation (a, b) and for nuclear fragmentation (c, d). The values are expressed as mean ±SEM (n=5).

This invention will be depicted in more detail by the following embodiments, but it is not to be considered that the range of this invention is limited by following embodiments.

DETAILED DESCRIPTION OF THE EMBODIMENTS

EXAMPLE 1

Aggregate formation and induction of apoptotic cell death by truncated DRPLA protein including expanded poluglutamine stretches.

Figure 1:
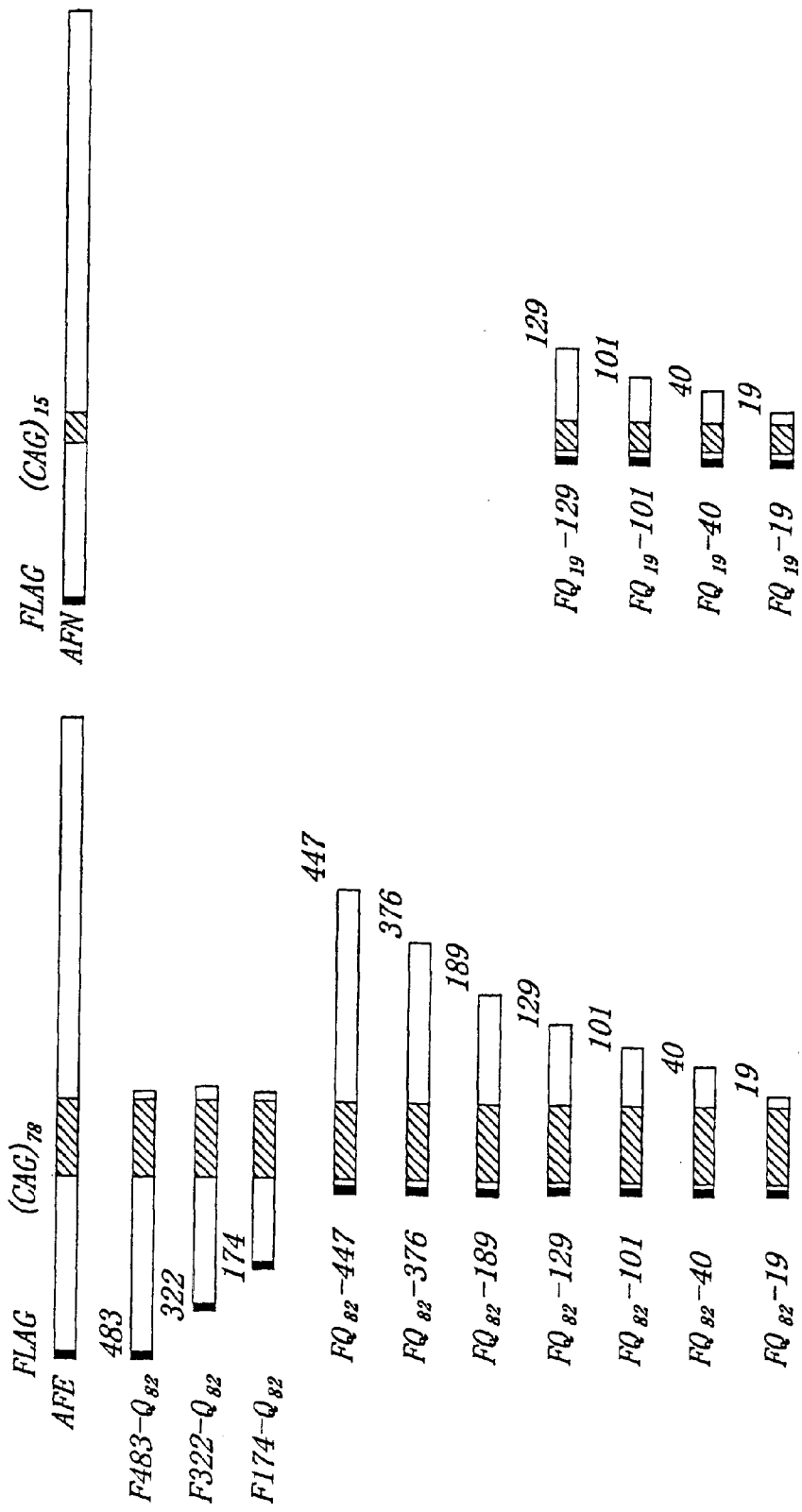
FIG. 1 shows the structures of the full-length DRPLA cDNAs and truncated DRPLA cDNAs with various lengths of deletions. The FLAG epitopes and the polyglutamine stretches are shown by filled boxes and hatched boxes, respectively. The protein coding sequences are shown by open boxes.

To investigate whether the full-length or truncated DRPLA mutant proteins exhibit structural abnormalities such as aggregate formation, or exhibit cytotoxicities, the inventors generated various deletion mutants of full-length wildtype (coding for 19 glutamines) and mutant (coding for 82 glutainines) DRPLA cDNAs (FIG. 1). Plasimids containing these cDNAs were constructed as below.

A full-length human DRPLA cDNA containing a CAG repeat of normal length (15 CAG repeats) (pDRPLAN) was constructed by ligating partial DRPLA cDNA clones (F1 and F15-20)[18] into a pBluescript SK(−) vector. A full-length human DRPLA cDNA containing an expanded CAG repeat (78 CAG repeats) (pDRPLAE) was constructed by replacing the 963-bp EcoT22I-SplI segment of pDRPLAN with the corresponding EcoT22I-SplI segment of a cosmid DRPLA genomic clone which was isolated from a genomic cosmid library constructed from genomic DNA of a patient with DRPLA. After the NotI-BbsI fragment of pDRPLAN, pDRPLAE or pDRPLA was removed, an oligonucleotide adapter containing the sequences for a NotI site, methionine, the FLAG tag and a BbsI site (5'-GCGGCCGCTCTAGAGCCGCCACCATGGACTAC AAAGACGATGACGACAAGATGAAGACAC-3') was ligated into a pBluescript SK(−) vector (pSK-AFN and pSK-AFE). The NotI-SalI fragment of pSK-AFN or pSK-AFE containing the segment coding for the translation initiation methionine, the FLAG tag and the entire DRPLA cDNA was subcloned into a mammalian expression vector, pEF-BOS[38] (pEF-BOS-AFN and pEF-BOS-AFE). Since there is a sequence of 5'-CAG-CAA-CAG-CAA upstream of the CAG repeat of the DRPLA cDNA (this segment is not included as the number of CAG repeats), pEF-BOS-AFN and pEF-BOS-AFE code for 19 and 82 glutamines, respectively.

Deletion mutants containing an expanded CAG repeat and a down-stream segment of various lengths were constructed. A segment containing 21 bp upstream of the CAG repeat, the CAG repeat and the 305 bp fragment downstream of the CAG repeat of pDRPLAN were first amplified by PCR using a primer (5'-GGCGGCCGCTCTAGAGCCGCCACCATG-GACTACAAAGACGATGACGACAAGCATCACCA CCAGCAACAGCAA-3') containing the sequences for the FLAG tag and a NotI linker, and a primer with the sequence 5'-ACCGGTGGGAAAGGGTAGGGC-3. The PCR products were digested with NotI and NarI, and then subcloned into pDRPLAE from which the corresponding NotI-NarI fragment had been removed (pBFE). Deletions of the segment downstream of the CAG repeat were generated either by ExoIII/Mung Bean nuclease digestion of pBFE, or by PCR using pDRPLAE as the template. The deleted DNA segments were subcloned into the pEF-BOS expression vector along with a multi-stop linker at the 3' end. The resultant plasmids, pEF-BOS-FQ$_{82}$-447, pEF-BOS-FQ$_{82}$-376, pEF-BOS-FQ$_{82}$-174, pEF-BOS-FQ$_{82}$-129, pEFBOS-FQ$_{82}$-101, pEF-BOS-FQ$_{82}$-40 and pEF-BOS-FQ$_{82}$-19, contain DNA segments coding for 3 histidines, 82 glutamines and various lengths of amino acids downstream of the polyglutamine stretch (447, 376, 174, 129, 101, 40 and 19 amino acids, respectively). Deletion mutants coding for 19 glutamines were also generated using similar methods.

Deletion mutants containing CAG repeats and the upstream segment of various lengths were constructed. DNA segments containing an expanded CAG repeat and upstream segments of various lengths were obtained by PCR using one of the following sense primers:
(A1FLAG, 5'-GGCGGCCGCTCTAGAGCCGCCACCATGGAC TACAAAGACGAT-GACGACAAGATGAAGACACGACAGAATAAA-3';

C1FLAG, 5'-GGCGGCCGCT-CTAGAGCCGCCACCATGGACTACAAA-GACGATGACGACAAGCCTCGACA GCCA-GAGGCTAGC-3'; or

C2FLAG, 5'-GGCGGCCGCTCTAGAGCCGCCACCATGGA-CTACAAAGACGATGACGACAAGCCACTACCTG GTCATCTGCCC-3') and an anti-sense primer (E8R: 5-GGGTCGACTTATCAGCCCTCCAGTGGGTGGG GAAAT-3'). The PCR products were digested by NotI and SalI, and subcloned into the pEF-BOS expression vector. The resultant plasmids, pEF-BOS-F483-Q$_{82}$, pEF-BOS-F322-Q$_{82}$ and pEF-BOS-F174-Q$_{82}$ contain the segments coding for the FLAG tag, 82 glutamines, 19 amino acids downstream of the polyglutamine stretch and upstream segments with 483, 322 and 174 amino acids upstream of the polyglutamine stretch, respectively.

The COS7 cells were transfected with plasmid thus constructed. COS7 cells were seeded in Dulbecco's modified Eagle's medium (DMEM) containing 10% fetal calf serum the day before transfection at 3×10$^4$ per well of an 8-well chamber slide (Nunc Inc., Naperville, Ill.). The COS7 cells were transfected with 0.5 μg of plasmid DNA using the SuperFect transfection reagent (Qiagen, Hilden, Germany) according to the manufacturer's instructions.

On the cells transfected with plasmid DNA, expression patterns of various DRPLA proteins described above were analyzed using anti-FLAG M5 monoclonal antibody 72 hours after transfection and the extent of apoptotic cell death was examined. Cells were fixed for 30 minutes in 4% paraformaldehyde in 0.1 M phosphate-buffered saline (PBS), permeabilized with PBS containing 0.02% Triton X-100, and incubated in 10% normal goat serum in PBS for 30 min at room temperature (RT). Cells were then incubated with an anti-FLAG M5 monoclonal antibody (Eastman Kodak, New Heaven, Conn.) with a 1:500 dilution for 2 hours at RT, followed by a 1 hour-incubation with rhodamine-conjugated anti-mouse IgG (Dako, Glostrup, Denmark) and observed by fluorescence microscopy.

Immunostaining using 3,3'-diaminobenzidine tetrahydrochrolide was also carried out using the avidin-biotin peroxidase complex (ABC) method. The cells were counterstained with hematoxylin and examined by light microscopy.

Figure 2A:
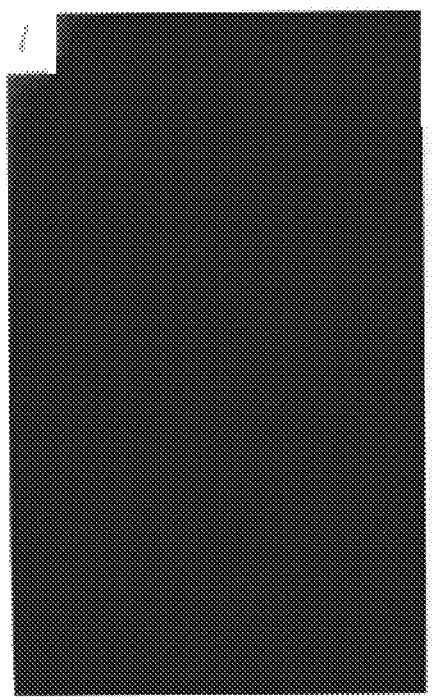
FIG. 2 shows immunocytochemical localization of full-length and truncated DRPLA proteins expressed in COS7 cells. COS7 cells were mock-transfected (a), or transfected with pEF-BOS-AFN (b), pEF-BOS-AFE (c), pEF-BOS-$FQ_{19}$-19 (d) or pEF-BOS-$FQ_{82}$-19 (e), followed by staining with an anti-FLAG M5 monoclonal antibody 72 hours after the transfection. These cells were detected by staining with rhodamine-conjugated anti-mouse Ig-G (e), or by the ABC method (f). These cells were stained positively in the TUNEL reaction using FITC-conjugated dUTP (g). Cells transfected with pEF-BOSS-AFE and pEGFP-Q82-19 were detected not only by GFP (h) but also by the anti-FLAG antibody (i). Percentages of cells with aggregate bodies (open box) and those stained in the TUNEL reaction among cells with aggregate bodies (filled box) are expressed as the mean±SEM (n=3) (j).
Figure 2B:
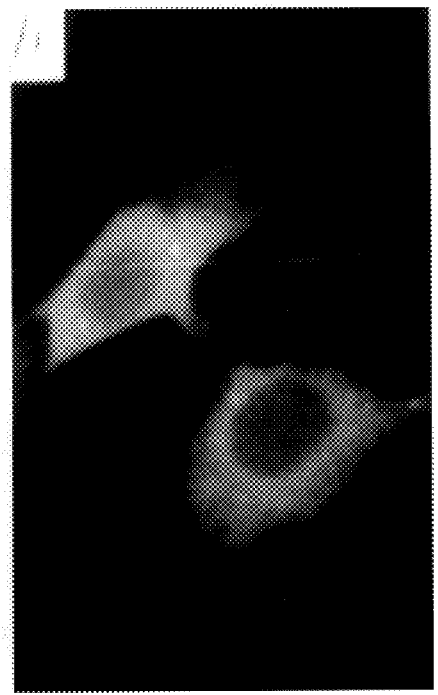
Figure 2C:
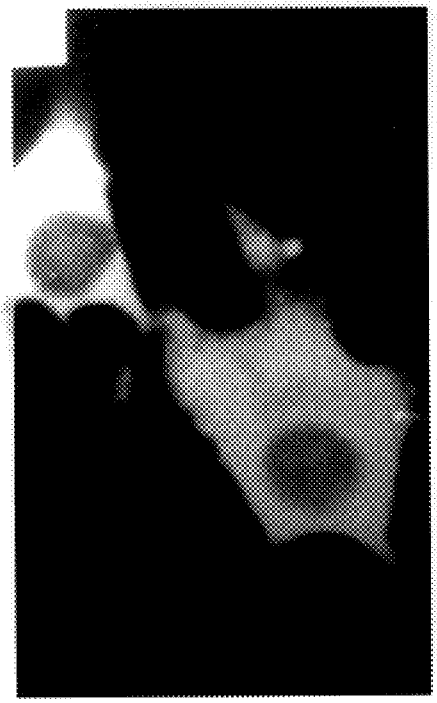
Figure 2D:
Figure 2E:
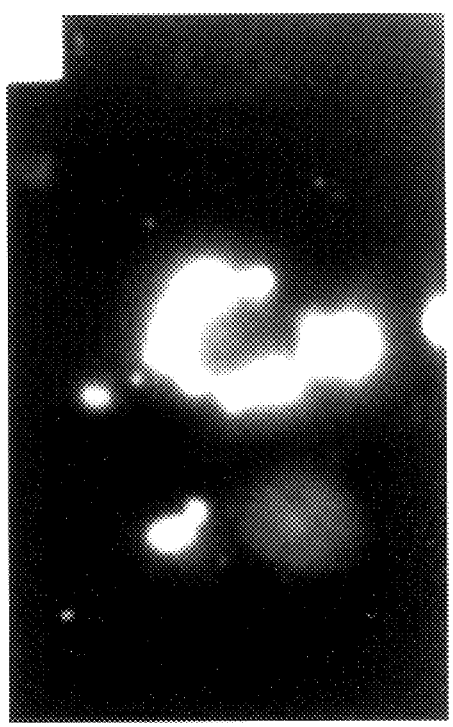
Figure 2F:
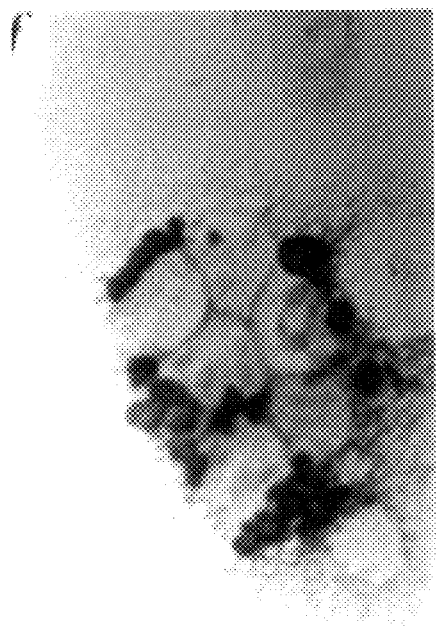
Figure 2G:

Cells transfected with pEF-BOS-AFN ecoding the full-length DRPLA protein containing a polyglutamine stretch of normal length (19 glutamines) expressed DRPLA protein diffusely in the cytoplasm with a homogenous or fine granular pattern (FIG. 2b), while mock-transfected cells were not stained by the antibody (FIG. 2a). Cells transfected with pEF-BOS-AFE coding for the full-length DRPLA protein with an expanded polyglutamine stretch (82 glutamines) (FIG. 2c) or cells transfected with pEF-BOS-FQ$_{19}$-19 coding for a truncated DRPLA protein containing mostly the polyglutamine stretch of normal length (19 glutamines) (FIG. 2d) also showed similar expression patterns to those of cells transfected with pEF-BOS-AFN (FIG. 2b). Cells transfected with pEF-BOSFQ$_{82}$-19 coding for a truncated protein containing mostly the expanded polyglutamine stretch (82 glutamines), however, showed distinct aggregate bodies mainly in the perinuclear cytoplasmic areas (FIGS. 2e,j). These aggregate bodies were immunopositive for ubiquitin in some population, but negative for vimentin or Congo red stain. With time, cells with these aggregate bodies became shrunken, and stained positively in the TUNEL (terminal deoxynucleotidyl-transferasemediated dUTP-biotinnick end-labeling) assay (FIG. 2g). These TUNEL-positive cells were observed frequently 72 hours after transfection (52% of the cells with aggregate bodies). On the other hand, apoptotic cells were not observed in cells transfected with pEF-BOS-AFN, pEF-BOS-AFE or pEF-BOS-FQ$_{19}$-19 (FIG. 2j).

To investigate whether full-length mutant DRPLA protein with the expanded polyglutamine stretch is incorporated into the aggregate bodies in the presence of aggregate bodies of truncated mutant proteins, another plasmid construct (pEGFP-Q$_{82}$-19) coding for the truncated mutant protein mostly containing the expanded polyglutamine stretch fused with GFP (green fluorescence protein) was made.

Figure 2H:
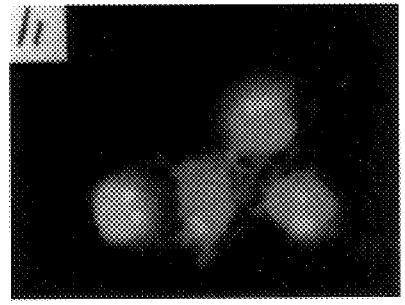
Figure 2I:
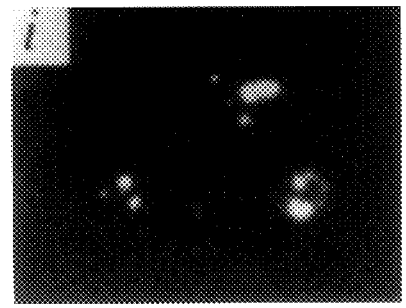
Figure 2J:
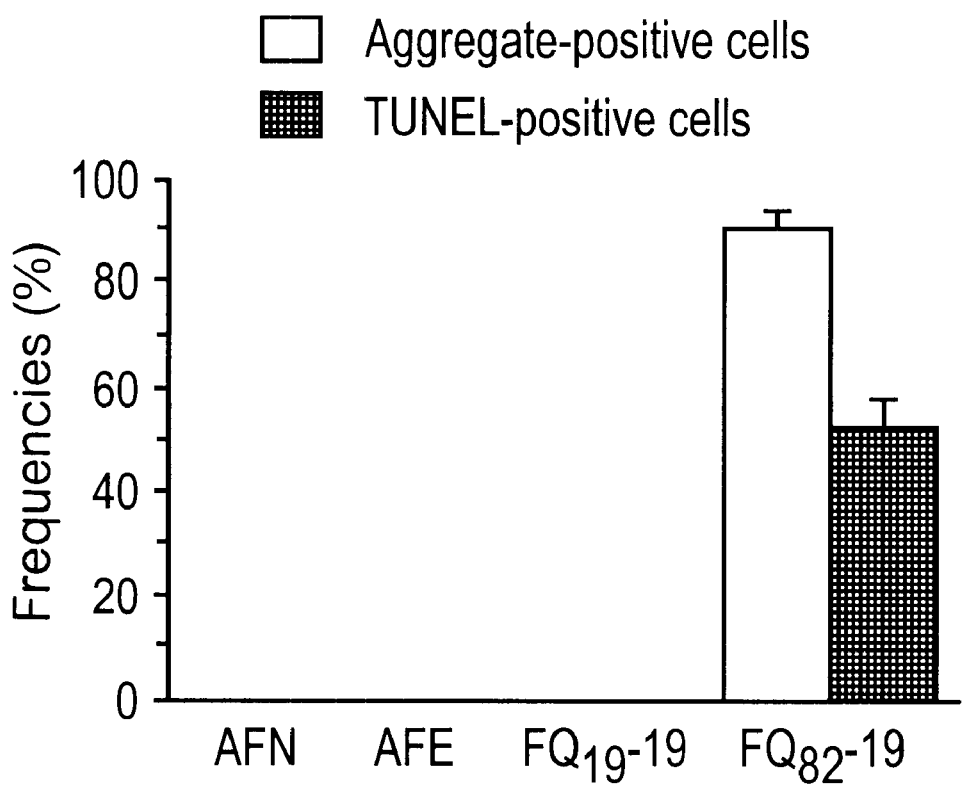

Incorporation of the full-length mutant FLAG-tagged DRPLA protein into the aggregate bodies was clearly demonstrated in cells co-transfected with pEF-BOS-AFE and pEGFP-Q$_{82}$-19 (FIGS. 2h, i). Such aggregation was never observed when the cells were transfected with pEF-BOS-AFE alone (FIG. 2c).

Figure 3:
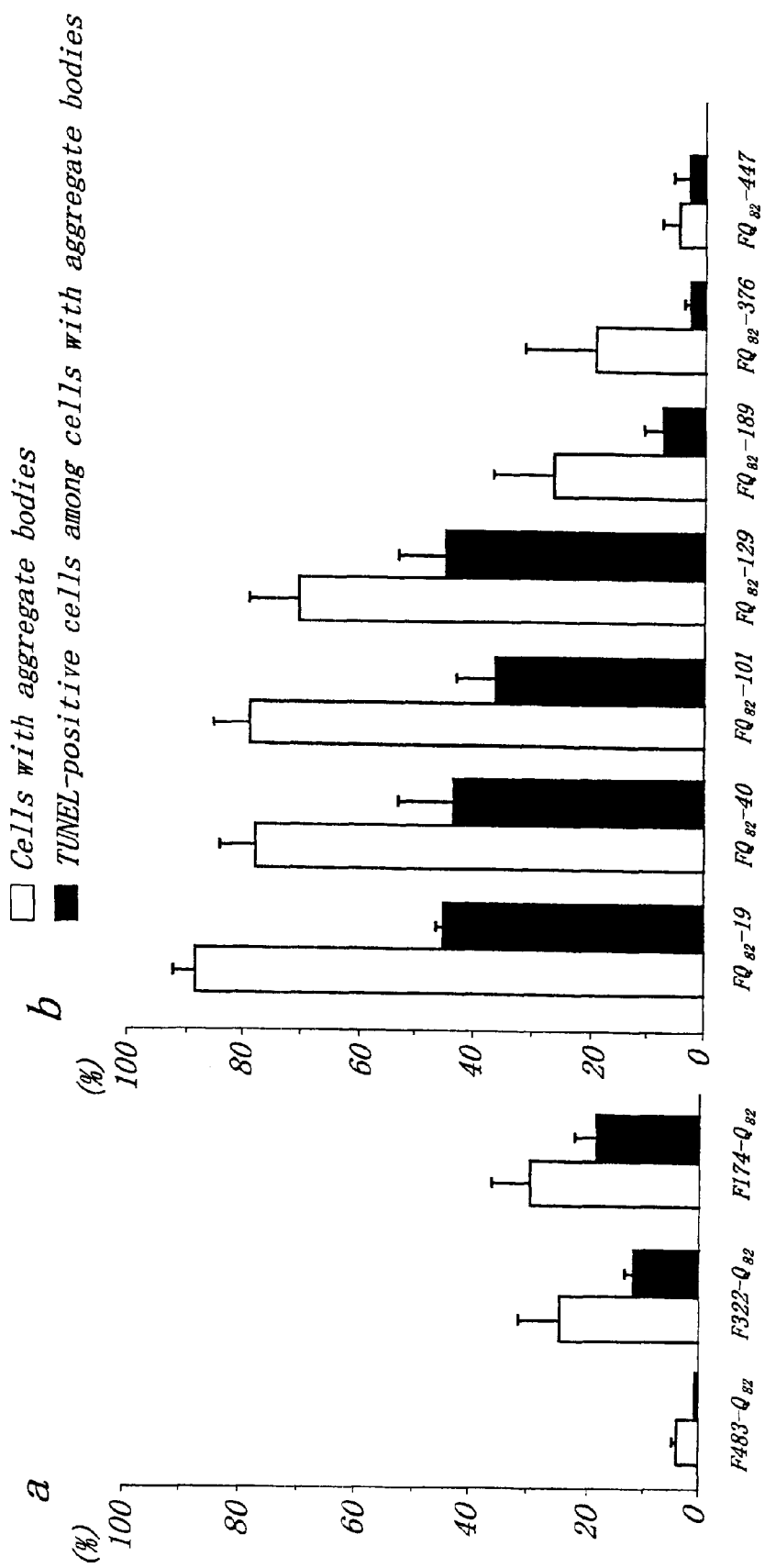
FIG. 3 shows percentages of cells exhibiting aggregate bodies and those stained in the TUNEL reaction among the cells with aggregate bodies. COS7 cells were transfected with pEGFP vectors containing various deletion mutants of DRPLA cDNA and assayed for the aggregate formation (open boxes) and the TUNEL reaction (filled boxes). The values are expressed as the mean±SEM (n=3).

To determine whether the formation of aggregate bodies is dependent on the lengths of the mutant proteins, the inventors generated various deletion mutants of the full-length wild-type and mutant DRPLA cDNAs (FIG. 1). Aggregate formation was observed at high frequencies (71–88%) in the cells expressing the truncated DRPLA proteins containing the polyglutamine stretch and the downstream region with 129 or fewer amino acids (FQ$_{82}$-129, FQ$_{82}$-101, FQ$_{82}$-40 or FQ$_{82}$-19) (FIG. 3b). Although the frequencies were low, aggregate formation was also observed in cells expressing various lengths of the upstream regions and the expanded polyglutamine stretch (F483-Q$_{82}$, F322-Q$_{82}$ or F174-Q$_{82}$) (FIG. 3a). The percentages of cells stained in the TUNEL reaction were high for cells transfected with pEF-BOS-FQ$_{82}$-129, pEF-BOS-FQ$_{82}$-101, pEF-BOS-FQ$_{82}$-40 or pEF-BOS-FQ$_{82}$-19. As cells formed aggregate bodies exhibited apoptotic cell death detected by TUNEL reaction, it was indicated strongly that formation of the aggregate bodies cause apoptotic cell death.

EXAMPLE 2

Time-dependent formation of aggregate bodies.

Figure 4A:
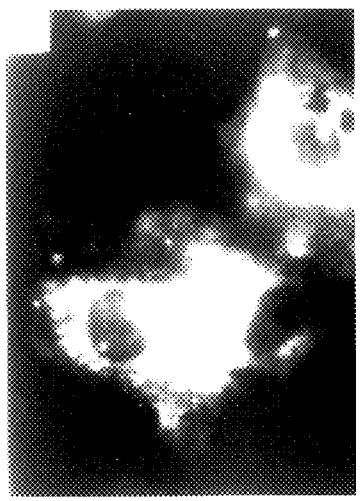
FIG. 4 shows time-dependent formation of aggregate bodies. COS7 cells were transfected with pEF-BOS-$FQ_{82}$-19 followed by immunocytochemical analysis using the anti-FLAG M5 monoclonal antibody. COS7 cells expressing the FLAG epitope at 24 hours after transfection (a), 48 and 72 hours after transfection, respectively (b, c). The ratios of cells that formed aggregate bodies and showed positive TUNEL reaction at each time (d). The values are expressed as the mean±SEM (n=3).
Figure 4B:
Figure 4C:
Figure 4D:
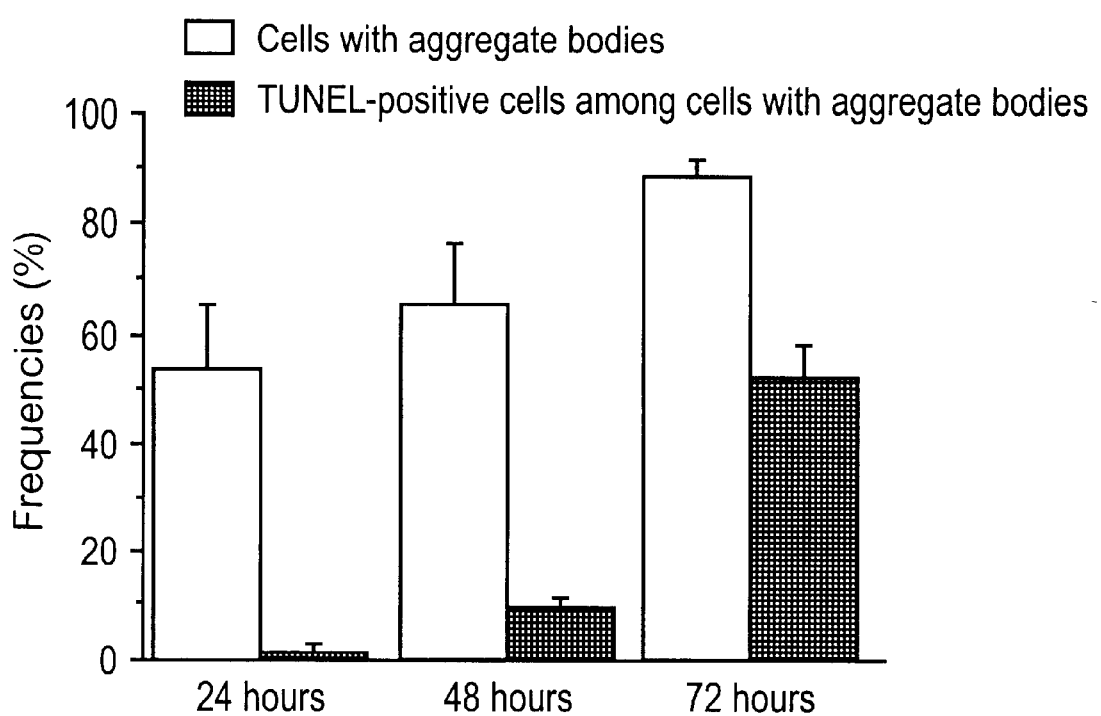

Time-dependent formation of aggregate bodies was examined. Imunohistochemical analysis was performed as described in EXAMPLE 1. Formation of the aggregate bodies was observed in 53% of the cells expressing the FLAG epitope at 24 hours after transfection with pEF-BOS-FQ$_{82}$-19 (FIGS. 4a, d). The percentage of cells exhibiting aggregate bodies increased to 65% (FIGS. 4b, d) and to 89% (FIGS. 4c, d) at 48 and 72 hours after the transfection, respectively. The frequency of TUNEL-positive cells was only 1% at 24 hours after transfection, but was increased to 9% and 52% at 48 and 72 hours after transfection, respectively (FIG. 4d).

EXAMPLE 3

Analysis on the detailed structures of aggregate bodies.

For the further analysis on the detailed structures of the aggregate bodies, the inventors observed the cells transfected with pEF-BOS-FQ$_{82}$-19 by electron microscopy. Cells were fixed with 4% paraformaldeheide-0.1% glutaraldehyde in 0.1M phosphate buffer, pH 7.4, for 15 min at RT. The cells were then dehydrated in a graded dimethylformamide series and embedded in LR White resin (London Resin Company, Berkshire, England). Ultrathin sections were cut and mounted on nickel grids. After incubation with 10% normal goat serum in PBS for 10 minutes at RT, the sections were incubated overnight at 4° C. with a mouse anti-FLAG M5 monoclonal antibody at a dilution of 1:4000. After washing with PBS, the sections were incubated with goat anti-mouse IgG conjugated to 10-nm gold (British BioCell International, Cardiff, UK; 1:30 dilution) for 30 min at RT. The sections were then washed with PBS and incubated in 2% glutaraldehyde in 0.1 M cacodylate buffer, pH 7.4. After washing with distilled water, the sections were stained with uranyl acetate and lead citrate, and examined with a Hitachi H-7100 electron microscope.

Figure 5A:
FIG. 5 shows electron microscopic findings of the aggregate bodies in the COS7 cells transfected with pEF-BOS-$FQ_{82}$-19. Immuno-electron microscopic study using the anti-FLAG M5 monoclonal antibody reveals that immunogold labels are associated with radially arranged filaments which form aggregates in a COS7 cell (a). The aggregates are formed infrequently in the nucleus but frequently in the perinuclear cytoplasm, and are composed of straight or slightly curved filaments approximately 10–12 nm in diameter (b, c). Penetration of the nuclear membrane by the aggregate-forming filaments was observed(c). Some of apoptotic bodies are engulfed by a neighboring cell (d). Scale bars=200 nm (a), 1 m (b), 400 nm (c) and 2 m (d).
Figure 5B:
Figure 5C:
Figure 5D:

Immuno-electron microscopic observation revealed that the aggregate bodies consist of fibrous aggregations mainly in perinuclear cytoplasmic areas (FIGS. 5a, b). The fibrous aggregations consist of radially oriented straight or slightly curved unbranched filaments approximately 10–12 nm in diameter (FIGS. 5b, c). No specific cell organella were found in the aggregates. These aggregate bodies were observed not only in the perinuclear areas in the cytoplasm but also occasionally in the nucleus (FIGS. 5b, c). Non-aggregated filaments with morphology similar to those of the aggregates were also scattered in the nuclei as well as in the cytoplasm. Penetration of the nuclear membrane by filaments of the aggregates, some of which were present via the nuclear pores, was often found in these cells (FIG. 5c). These filamentous structures were observed only in cells transfected with pEF-BOS-FQ$_{82}$-19, but not in cells transfected with pEF-BOS-AFN, pEF-BOS-AFE or pEF-BOS-FQ$_{19}$-19. With culture time after transfection, many apoptotic bodies containing the aggregates were encountered (FIG. 5d).

EXAMPLE 4

Detection of intranuclear inclusions in cerebellar dentate nucleus of DRPLA patients.

Figure 6A:
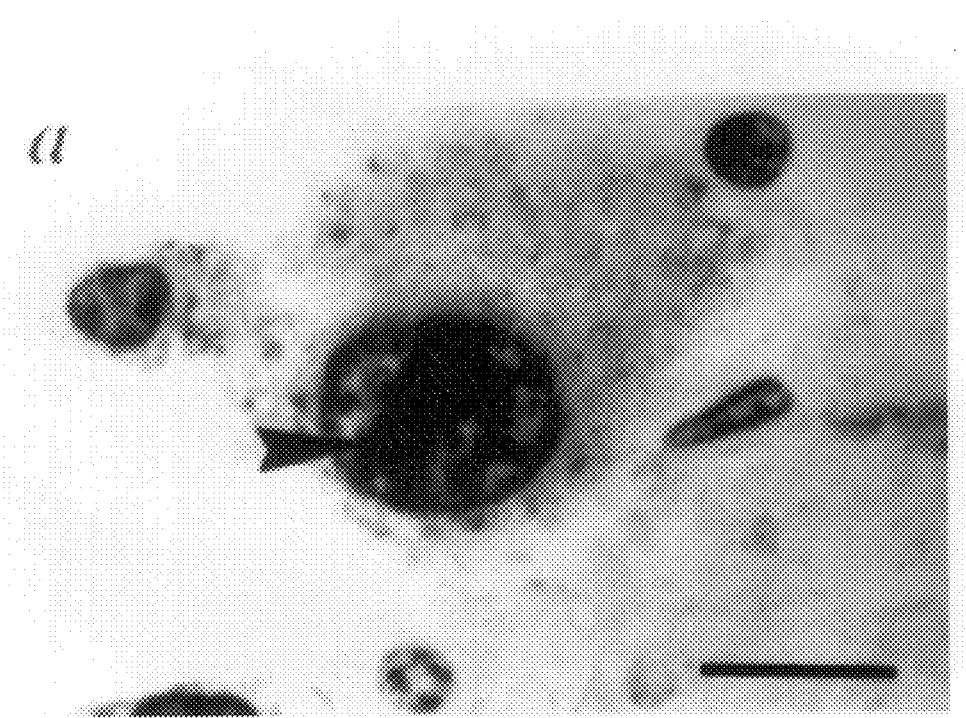
FIG. 6 shows intranuclear inclusions in dentate nucleus of DRPLA cerebellum. Neuronal intranuclear inclusions in the cerebellar dentate nuclei of DRPLA patients were stained by an anti-DRPLA protein polyclonal antibody raised against residues 172–253 of DRPLA protein (a). The inclusions were also stained by an anti-ubiquitin antibody (b). Electron microscopic observation (c). Scale bars=1 m (a, b, c). The intranuclear inclusions are indicated by arrow heads.
Figure 6B:
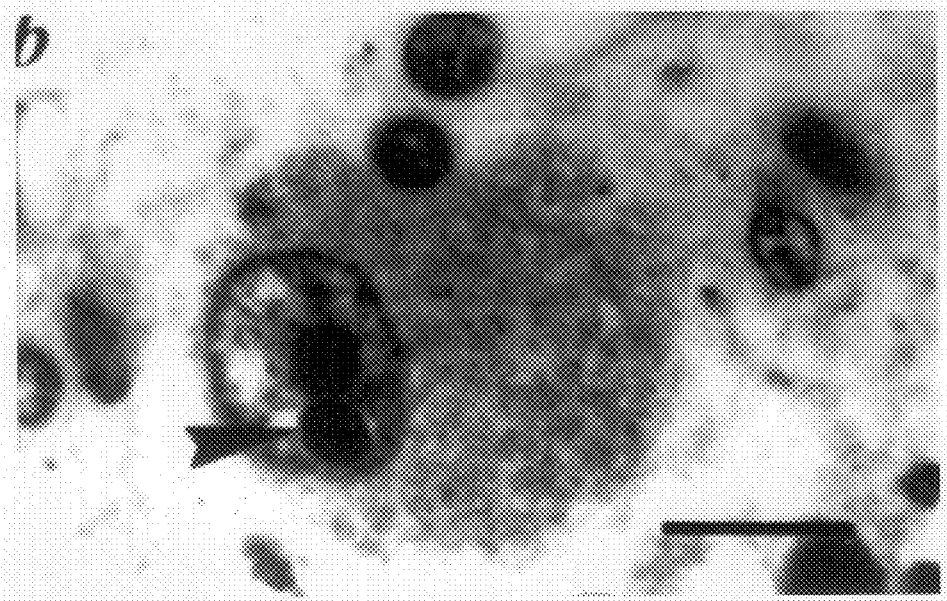

To investigate if similar aggregates were present in the brains of DRPLA patients, the inventors performed immunohistochemical analysis of the dentate nucleus in the cerebellum of DRPLA patients (n=5) and controls (n=5) using an anti-DRPLA protein polyclonal antibody. The autopsied brains were fixed with phosphate-buffered 4% paraformaldehyde and embedded in paraffin for histological examination. Immunostaining was performed using a rabbit antiubiquitin antibody (Dakopatts: 1:200 dilution) or a rabbit anti-DRPLA protein polyclonal antibody (1:300 dilution), which was generated against a GST-fusion protein containing amino acid residues 172–253 of DRPLA protein and affinity-purified using an Affigel-10 column (Bio-Rad) conjugated with the GST-fusion protein. Presence of intranuclear inclusions, which were stained with the anti-DRPLA protein antibody (FIG. 6a) as well as with an anti-ubiquitin antibody (FIG. 6b), was confirmed in all the 5 DRPLA patients. Such inclusions were never observed in the controls.

Figure 6C:
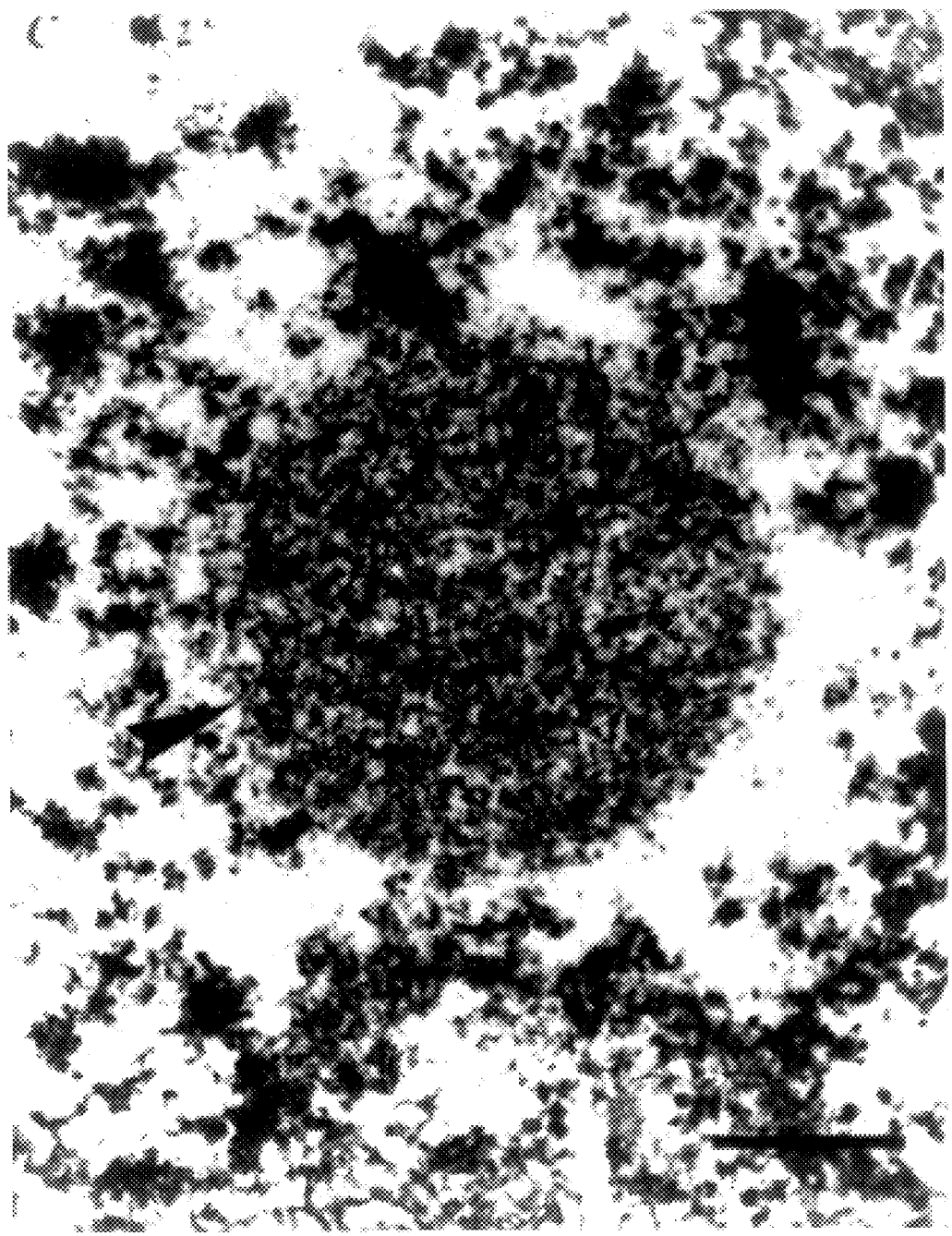

The intranuclear inclusions were examined by electron microscope. Cells were fixed with 3% glutaraldehyde-1% paraformaldeheide in 0.1 M phosphate buffer, pH 7.4, post-fixed in 1% osmium tetroxide, dehydrated in a graded ethanol series and embedded in Epon 812. Ultrathin sections were cut and stained with uranyl acetate and lead citrate, and examined with a Hitachi H-7100 electron microscope. Electron microscopic study revealed that the intranuclear inclusions were composed of fine granular and occasionally filamentous structures (FIG. 6c). These results indicate the possibility that formation of intranuclear inclusions play a important role at onset of neurodegenerative diseases.

EXAMPLE 5

Suppression of aggregate formation and apoptotic cell death by transglutaminase inhibitors.

To investigate whether the transglutaminase reaction is involved in the formation of aggregate bodies and the induction of apoptotic cell death, the inventors cultured COS7 cells in the presence of transglutaminase inhibitors (cystamine[28], monodansyl cadaverine (MDC)[29], and putrescine[30]), after transfection. For tilis purpose, truncated DRPLA proteins were expressed as fusion proteins with green fluorescence protein (GFP), which allowed the highly sensitive observation of viable cells. The inserts of pEF-BOS-FQ$_{82}$-19 and pEF-BOS-FQ$_{19}$-19 were transferred into pEGFP containing the coding region for GFP. The resultant plasmid DNAs (pEGFP-FQ$_{82}$-19 and pEGFP-FQ$_{19}$-19) were transfected into COS7 cells. The plasmid DNA was constructed as below. The segment coding for 3 histidines, the polyglutamine stretch and 19 amino acids downstream of the polyglutamine stretch of DRPLA cDNA (pDRPLAE or pDRPLAN) was amplified by PCR using a primer (5'-GGGAATTCGGATGCACCAT-CACCACCAGCAACAGCAACAG-3') containing an EcoRI linker sequence and a primer (5'-GTGGATCCCCGCCCTCCAGTGGGTGGGGAAATGCT-3'). PCR products were digested with EcoRI and BamHI, and subcloned into the pEGFP-N1 expression vector (Clontech, Palo Alto, Calif.). The nucleotide sequences of all the constructs were confirmed using automated DNA sequencers (PE Applied Biosystems, Foster City, Calif.).

Figure 7A:
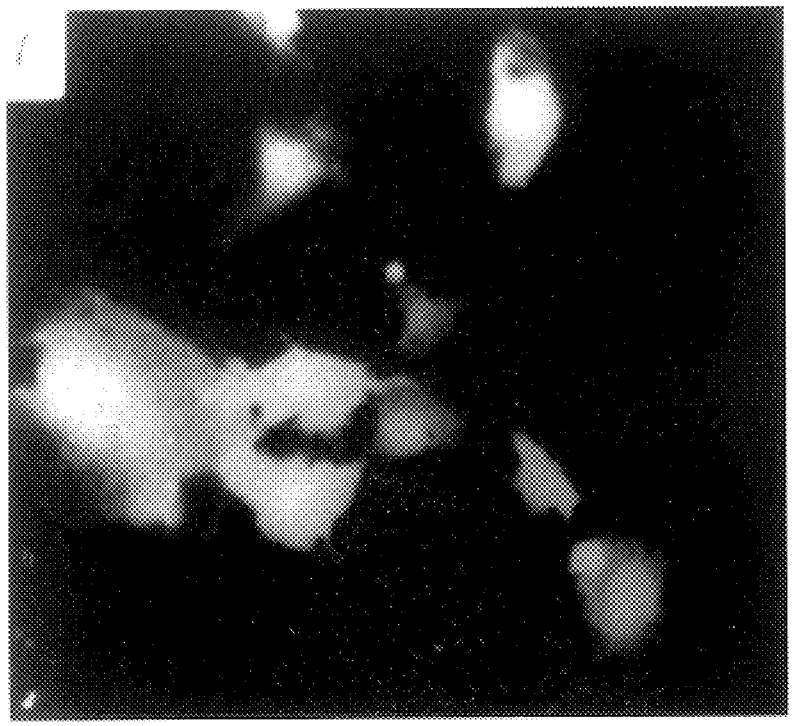
FIG. 7 shows effect of cystamine on the aggregate formation and apoptotic cell death of COS7 cells transfected with pEF-BOS-$Q_{82}$-19. COS7 cells transfected with pEGFP-$FQ_{19}$-19 or pEGFP-$FQ_{82}$-19 were cultured in the presence or absence of 1 mM cystamine for 60 hours, and observed for the aggregate formation and nuclear fragmentation as detected by staining with Hoechst 33342. The pictures show cells transfected with pEGFP-$FQ_{19}$-19 in the absence (a) or presence (b) of 1 mM cystamine, and cells transfected with pEGFP-$Q_{82}$-19 in the absence (c) or presence (d) of 1 mM cystamine. (e) Effect of cystamine on the level of formation of aggregate bodies and nuclear fragmentation in COS7 cells transfected with pEGFP-$Q_{82}$-19. (f) Effect of cystamine on the level of nuclear fragmentation of COS7 cells transfected with pEGFP-$Q_{82}$-19. The values are expressed as the mean±SEM (n=5).
Figure 7B:
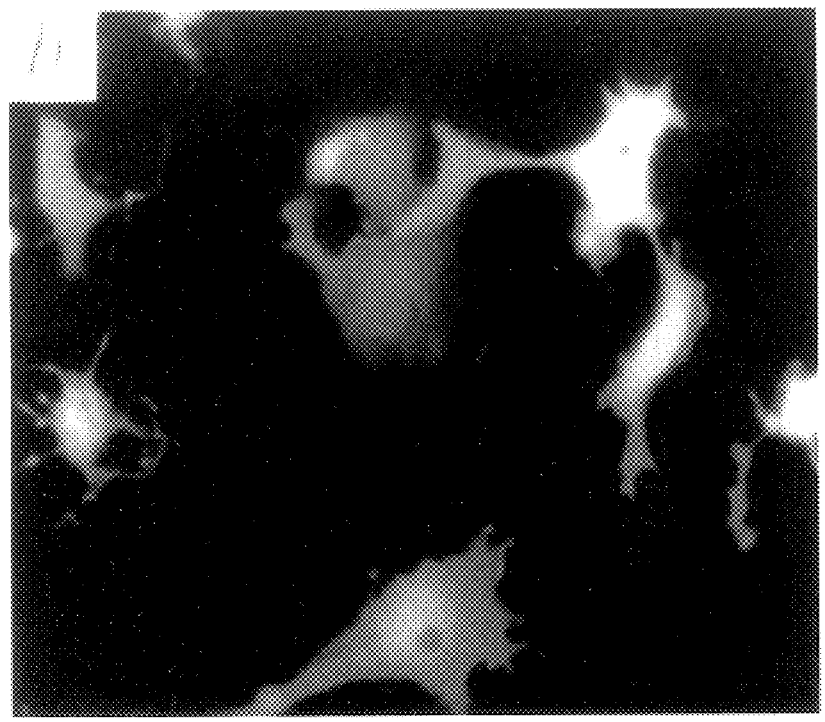
Figure 7C:
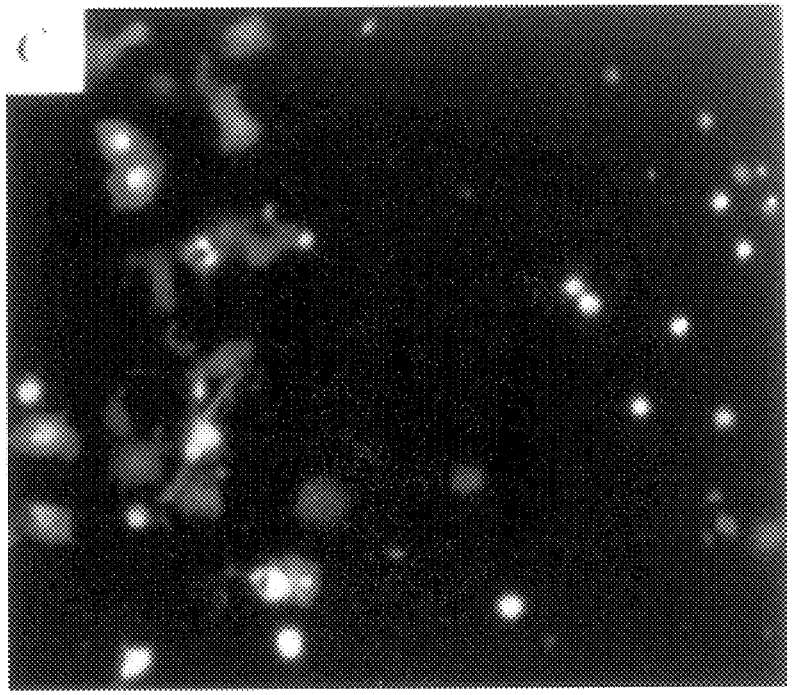
Figure 7D:
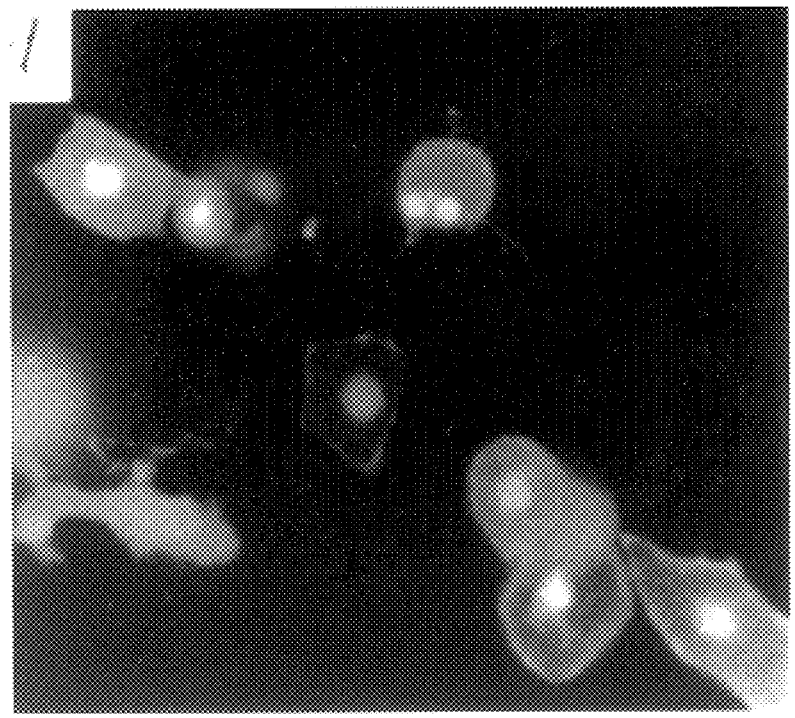
Figures 7E, 7F:
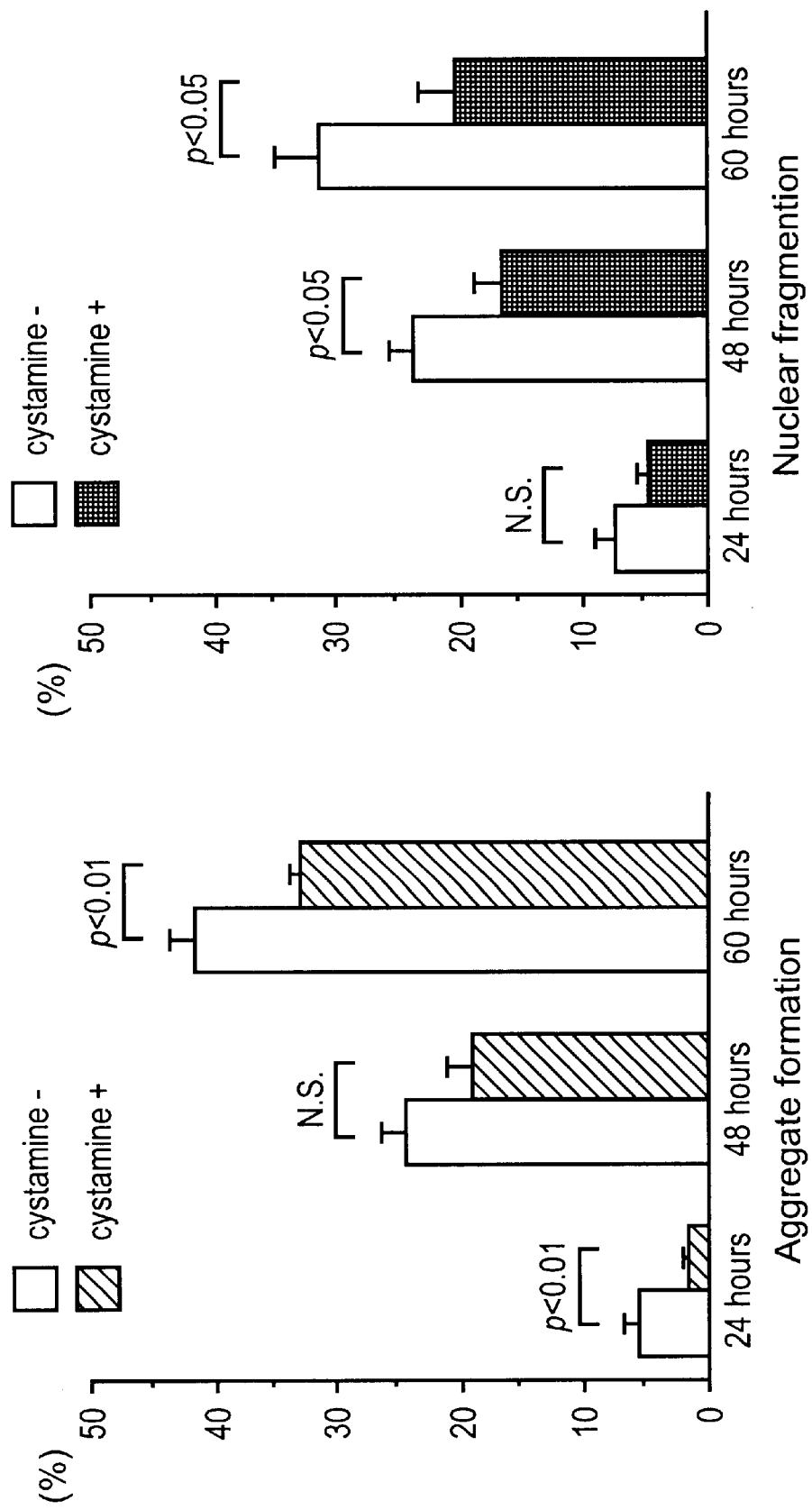

Cells transfected with pEGFP-Q$_{19}$-19 expressed the GFP fusion protein diffusely in the cytoplasm (FIG. 7a), wlile cells transfected with pEGFP-Q$_{82}$-19 exhibited formation of aggregate bodies (FIG. 7c), similarly to those transfected with pEF-BOS-FQ$_{19}$-19 and pEF-BOS-FQ$_{82}$-19, respectively. Cystamine did not change the expression patterns of the fusion protein in the pEGFP-Q$_{19}$-19-transfected cells (FIG. 7b). When the cells transfected with pEGFP-Q$_{82}$-19 were cultured for 60 hours in 1 mM cystamine, however, formation of aggregate bodies was significantly suppressed from 42% to 33% ($P<0.01$) (FIGS. 7c, d, e). Nuclear fragmentation was also suppressed from 38% to 24% in the presence of 1 mM cystamine ($P<0.05$) (FIG. 7f). Similar results were observed at 24 and 48 hours after transfection (FIGS. 7e, f). On the other hand, the frequency of cells retaining a diffuse cytoplasmic expression pattern without aggregate formation was increased from 32% (absence of cystamine) to 56% (1 mM cystamine) at 60 hours after transfection ($P<0.01$). The suppression of aggregate bodies and nuclear fragmentation was observed even at 100 M of cystamine and the suppression effects appeared in a dose-dependent manner (FIGS. 8a, c).

The effects of other transglutaminase inhibitor (MDC) on the aggregate formation and apoptotic cell death were also investigated. The TUNEL assay was performed using an In Situ Cell Death Detection Kit (Boehringer Mannheim, Mannheim, Germany) according to the manufacturer's instructions. FITC-conjugated dUTP was used for the terminal deoxynucleotidyl transferase reaction. An assay for nuclear fragmentation was performed by staining cells with 5 M Hoechst 33342. Quantitation was performed by analyzing 100 cells expressing the FLAG epitope. Statistical analyses were performed using Student's t test.

Strong suppression of nuclear fragmentation by MDC was observed in a dose dependent manner (FIG. 8d). There were no significant changes in the frequencies of the cells with aggregate formation (FIG. 8b), although the sizes of the aggregate bodies were smaller when the transfected cells were cultured in the presence of MDC compared to those observed in the absence of MDC.

REFERENCES

1. La Spada, A. R., Wilson, E. M., Lubahn, D. B., Harding, A. E. & Fischbeck, K. H. Androgen receptor gene mutations in X-linked spinal and bulbar muscular atrophy. *Nature* 352, 77–79 (1991).
2. The Huntington's Disease Collaborative Research Group. A novel gene containing a trinucleotide repeat that is expanded and unstable on huntington's disease clromosomes. *Cell* 72, 971–983 (1993).
3. Orr, H. T. et al. Expansion of an unstable trinucleotide CAG repeat in spinocerebellar ataxia type 1. *Nature Genet.* 4, 221–226 (1993).
4. Koide, R. et al. Unstable expansion of CAG repeat in hereditary dentatorubral-pallidoluysian atrophy (DRPLA). *Nature Genet.* 6, 9–13 (1994).
5. Nagafuchi, S. et al. Expansion of an unstable CAG trinucleotide on chromosome 12p in dentatorubral and pallidoluysian atrophy. *Nature Genet.* 6, 14–18 (1994).
6. Kawaguchi, Y. et al. CAG repeat expansion in a novel gene for Machado-Joseph disease at chromosome 14q32.1. *Nat Genet.* 8, 221–227 (1994).
7. Sanpei, K. et al. Identification of the spinocerebellar ataxia type 2 gene using a direct identification of repeat expansion and cloning technique, DIRECT. *Nature Genet.* 14, 277–284 (1996).
8. Pulst, S. M. et al. Moderate expansion of a normally biallelic trinucleotide repeat in spinocerebellar ataxia type 2. *Nature Genet.* 14, 269–276 (1996).
9. Imbert, G. et al. Cloning of the gene for spinocerebellar ataxia 2 reveals a locus with high sensitivity to expanded CAG/glutamine repeats. *Nature Genet.* 14, 285–291 (1996).
10. Zhuchenko, O. et al. Autosomal dominant cerebellar ataxia (SCA6) associated with small polyglutamine expansions in the alpha 1a-voltage-dependent calcium channel. *Nature Genet.* 15, 62–69 (1997).
11. David, G. et al. Cloning of the SCA7 gene reveals a highly unstable CAG repeat expansion. *Nature Genetics.* 17, 65–70 (1997).
12. Lubahn, D. B. et al. Cloning of human androgen receptor complementary DNA and localization to the x chromosome. *Science* 240,327–330 (1988).
13. Nagafuchi, S. et al. Structure and expression of the gene responsible for the triplet repeat disorder, dentatorubral and pallidoluysian atrophy (DRPLA). *Nature Genet.* 8, 177–182 (1994).
14. Mori, Y. et al. Primary structure and functional expression from complementary DNA of a brain calcium channel. *Nature* 350, 398–402 (1991).
15. Yazawa, I. et aL Abnormal gene product identified in hereditary dentatorubral-pallidoluysian atrophy (DRPLA) brain. *Nature Genet.* 10, 99–103 (1995).
16. Trottier, Y. et al. Cellular localization of the huntington's disease protein and discrimination of the normal and mutated form. *Nature Genet.* 10, 104–110 (1995).
17. Servadio, A. et al. Expression analysis of the ataxin-1 protein in tissues from normal and spinocerebellar ataxia type 1 individuals. *Nat Genet.* 10, 94–98 (1995).
18. Onodera, O. et al. Molecular cloning of a full-length cDNA for dentatorubral-pallidoluysian atrophy and regional expressions of the expanded alleles in the CNS. *Am. J. Hum. Genet.* 57, 1050–1060 (1995).
19. Burright, E. N. et al. SCA1 transgenic mice: a model for neurodegeneration caused by an expanded CAG trinucleotide repeat. *Cell* 82, 937–948 (1995).
20. Ikeda, H. et al. Expanded polyglutamine in the Machado-Joseph disease protein induces cell death in vitro and in vivo. *Nature Genet.* 13, 196–202 (1996).
21. Mangiarini, L. et al. Exon 1 of the HD gene with an expanded cag repeat is sufficient to cause a progressive neurological phenotype in transgenic mice. *Cell* 87, 493–506 (1996).
22. Davies, S. W. et al. Formation of neuronal intranuclear inclusions underlies the neurological dysfunction in mice transgenic for the HD mutation. *Cell* 90, 537–548 (1997).
23. Perutz, M. F., Johnson, T., Suzuki, M. & Finch, J. T. Glutamine repeats as polar zippers: their possible role in inherited neurodegenerative diseases. *Proc. Natl. Acad. Sci. USA* 91, 5355–5358 (1994).
24. Stott, K., Blackburn, J. M., Butler, P. J. & Perutz, M. F. Incorporation of glutamine repeats makes protein oligomerize: implications for neurodegenerative diseases. *Proc. Natl. Acad. Sci. USA* 92, 6509–6513 (1995).
25. Kahlem, P., Terre, C., Green, H., & Djian, P. Peptides containing glutamine repeats as substrates for transglutaminase-catalyzed cross-linking: relevance to diseases of the nervous system. *Proc. Natl. Acad. Sci. USA* 93, 14580–14585 (1996).
26. Naito, H. & Oyanagi, S. Familial myoclonus epilepsy and choreoathetosis: hereditary dentatorubral-pallidoluysian atrophy. *Neurol.* 32, 798–807 (1982).
27. Ikeuchi, T. et al. Dentatorubral-pallidoluysian atrophy (DRPLA): Clinical features are closely related to unstable expansions of trinucleotide (CAG) repeat. *Ann. Neurol.* 37, 769–775 (1995).
28. Lorand, L. et al. Specificity of guinea pig liver transglutaminase for amine substrates. *Biochemistry* 18, 1756–1765 (1979).
29. Dickson, R. B., Willingham, M. C., & Pastan, I. Binding and internalization of $^{125}$I-$\alpha_2$-macroglobulin by cultured fibroblast. *J. Biol. Chem.* 256, 3454–3459 (1981).
30. Kleman, J.-P., Aeschlimann, D., Paulsson, M. & van der Rest, M. Transglutaminase-catalyzed cross linking of fibrils of collagen V/XI in A 204 rhabdomyosarcoma cell. *Biochemistry* 34, 13768–13775 (1995).
31. Paulson, H. L. et al. Intranuclear inclusions of expanded polyglutamine protein in spinocerebellar ataxia type 3. *Neutron* 19, 333–334 (1997).
32. Scherzinger, E., et al. Huntingtin-encoded polyglutamine expansions form amyloid-like protein aggregates in vitro and in vivo. *Cell* 90, 549–558 (1997).
33. Onodera, O. et al. Oligomerization of expanded-polyglutamine domain fluorescent fusion proteins in cultured mammalian cells. *Biochem.Biophy. Res. Commun.*, (In the press).
34. Jackson, M., et al. The cortical neuritic pathology of Huntington's disease. *Neuropathol. Appl. Neurobiol.* 21, 18–26 (1995).
36. DiFiglia, M. et al. Aggregation of Huntingtin in neuronal intranuclear inclusions and dystrophic neulites in brain. *Science* 277, 1990–1993 (1997).
37. Paulson, H. L. et al. Machado-Joseph disease gene product is a cytoplasmic protein widely expressed in brain. *Ann. Neurol.* 41, 453–462 (1997).
38. Goldberg, Y. P. et al. Cleavage of huntingtin by apopain, a proapoptotic cysteine protease, is modulated by the polyglutamine tract. *Nature Genet.* 13, 442–449 (1996).
39. Mizusliima, S. & Nagata, S. pEF-BOS, a powerful mammalian expression vector. *Nucleic Acids Res.* 18, 5322 (1990).

What is claim is:

1. A method of treating a CAG repeat expansion disease comprising administering a therapeutically effective amount of a pharmaceutical composition comprising a transglutaminase inhibitor, wherein the transglutaminase inhibitor is selected from a group consisting of cystamine and monodanysl cadaverine.

2. A method of treating a CAG repeat expansion disease comprising administering a therapeutically effective amount of a pharmaceutical composition for treating a CAG repeat expansion disease, said pharmaceutical composition comprising a transglutaminase inhibitor as its ingredient, and at least one pharmaceutically accepted ingredient for formulation.

3. The method of claim 1, wherein the CAG repeat expansion disease is selected from a group consisting of: spinal and bulbar muscular atrophy, Huntington's disease, spinocerebellar ataxia type1, dentatorubral-pallidoluysian atrophy, Machado-Joseph disease, spinocerebellar ataxia 2, spinocerebellar ataxia 6 and spinocerebellar ataxia 7.

* * * * *